US006218347B1

(12) United States Patent
Rau et al.

(10) Patent No.: US 6,218,347 B1
(45) Date of Patent: Apr. 17, 2001

(54) CLEANSING BAR WITH FILLER AND EXCELLENT AESTHETIC PROPERTIES

(75) Inventors: Allen H. Rau, Cincinnati, OH (US); Vincent J. Fischer, Cold Spring, KY (US); Gregory A. Freeman, Mason; Mary A. Schwartz, Hamilton, both of OH (US)

(73) Assignee: The Andrew Jergens Company, Cincinnati, OH (US)

( * ) Notice: Subject to any disclaimer, the term of this patent is extended or adjusted under 35 U.S.C. 154(b) by 0 days.

(21) Appl. No.: 09/520,212

(22) Filed: Mar. 7, 2000

Related U.S. Application Data

(62) Division of application No. 08/938,885, filed on Sep. 26, 1997, now Pat. No. 6,074,997.

(51) Int. Cl.[7] ................................ A61K 7/48; A61K 7/50

(52) U.S. Cl. .......................... 510/151; 510/153; 510/155; 510/156; 510/474

(58) Field of Search .................................... 510/151, 153, 510/155, 156, 474

(56) References Cited

U.S. PATENT DOCUMENTS

| | | | | |
|---|---|---|---|---|
| 4,692,261 | * | 9/1987 | Filomeno | 252/105 |
| 4,941,990 | * | 7/1990 | McLaughlin | 252/121 |
| 5,691,287 | * | 11/1997 | Villars et al. | 510/151 |
| 5,756,438 | * | 5/1998 | Rau et al. | 510/151 |

* cited by examiner

*Primary Examiner*—Necholus Ogden
(74) *Attorney, Agent, or Firm*—Piper Marbury Rudnick & Wolfe LLP; Steven B. Kelber

(57) ABSTRACT

A non-soap cleansing bar of superior lathering, feel and aesthetic characteristics is prepared with a quaternary ammonium surfactant, an anionic surfactant, a waxy binder, a filler and water. The balance of components is maintained so that the mixture can be formed on conventional plodding equipment. Optional elements, such as fragrances, preservatives, colorants, emollients and the like can be added.

11 Claims, No Drawings

CLEANSING BAR WITH FILLER AND EXCELLENT AESTHETIC PROPERTIES

This application is a division of application Ser. No. 08/938,885 filed on Sep. 26, 1997 U.S. Pat. No. 6,074,997.

BACKGROUND OF THE INVENTION

1. Field of the Invention

This invention pertains to a solid cleansing composition, of the general type and shape of a cleansing bar. A solid cleansing bar is provided with high filler loading, and simultaneously excellent lathering, texture, feel characteristics and aesthetics. The bar can be produced by conventional plodding technology, and yet exhibits superior properties when compared with related technology prepared according to tableting processes which are not nearly as productive.

2. Background of the Prior Art

U.S. patent application Ser. No. 08/621,965, filed Mar. 26, 1996, now U.S. Pat. No. 5,756,438, the entirety of which is incorporated herein by reference, discloses cleansing bars containing a high proportion of fillers, in particular fillers such as maltodextrin or dextrose. Other fillers, including other carbohydrates, starches and dextrins, as well as inorganic particulate fillers such as talc, kaolin, bentonite clay, carbonate or sulphate salts, sugars and crystalline polyols are noted. The filler is combined with a surfactant system which includes anionic surfactants, and/or non-ionic surfactants, which may be used together with zwitterionic and cationic surfactants. While this patent application describes the potential use of quaternary ammonium chlorides, use of the same is not exemplified. One problem with using such quaternary surfactants is the pH level generally encountered in solid cleansing products, even non-soap cleansing products of the type addressed herein and in the referenced pending application. Specifically, a neutral-alkaline pH may generate, through decomposition, free amines, and the associated unpleasant odor as well as product discoloration. Additionally, many commercially available quaternary surfactant compositions comprise residual free amines.

U.S. Pat. No. 5,756,438 describes a process for production that involves melting a waxy binder, mixing it with the remaining components and subsequently tableting the so processed mass. While the processing specified gives rise to a highly desirable product, it is specifically disclosed that the high production techniques generally used in bar products, referred to as "plodding", cannot be used. This necessarily imparts significant costs to the process of manufacture.

Other highly filled bar products have been attempted, but are generally inadequate in one or more important product considerations. These include lathering, or foaming. In general, the presence of a high degree of filler complicates the ability to produce adequate foaming. Another essential aspect of the product is its feel or texture. The higher proportion of filler typically gives rise to a "dragging" or "rough" feeling in the bar itself. Similarly, the product must be aesthetically pleasing. Commercial products with a high filler loading provide an unattractive bar, that cracks or splinters quickly upon use, and/or presents a grainy, pebbled surface.

Japanese Kokai 56-84798, published Jul. 10, 1981, is directed to a soap composition which contains, by weight, 60–90% starch or cellulose. Unlike the non-soap product of U.S. Pat. No. 5,756,438, and the claimed invention, the Kokai is directed to a granular soap which is a compacted powder intended to achieve rapid disintegration, and through disintegration, washing. The product is intended for use as a tablet which disintegrates upon admixture with water. Thus, while other high-filler compositions are known, none provide a suitable combination of acceptable lathering performance, acceptable filler texture, aesthetic properties and ease of manufacturing. The provision of a personal, non-soap cleansing bar, meeting these goals, continues to be an object of those of skill in the art.

SUMMARY OF THE INVENTION

The above objects, and others explained in more detail below, are met by the provision of a non-soap solid cleansing bar which can be prepared on conventional plodding machines, which includes as essential components a surfactant including an anionic surfactant, and fillers. Fillers are present in amounts of about 45–80% by weight, anionic surfactants are present in an amount of about 15–45% by weight, quaternary surfactants are present in amounts of about 0–5% by weight and waxy binder materials are present in an amount of about 0–20% by weight. The resulting product exhibits superior lathering, is prepared by conventional plodding processing, and has excellent aesthetic and texture properties. The bar exhibits a pH below about 7.0, that is an acidic pH, generally about 4–6.5. This suppresses the generation of amine odors due to the presence of the quaternary surfactant. The cleansing bar further incorporates a minimum 5% by weight water. Water may be present in amounts up to about 20% by weight.

DETAILED DESCRIPTION OF THE INVENTION

This invention is described, in detail, below. All percentage values recited are active ingredient percentage by weight. Percentages, where recited, are approximate, unless indicated to the contrary. It is not the precise numerical value of the percentage recited, unless so indicated, but rather the balance of components selected so as to achieve the performance characteristics demonstrated, with ease of mechanical preparation, that characterize the claimed invention.

The invention is a personal non-soap cleansing bar. While shape and size is not unduly restricted, it is intended for, and must be acceptable for use by human hands or acceptable cleansing accessory (puffs, sponges, loofahs and the like), over an extended wear period with multiple uses. The product typically weighs between 1 and 10 ounces, and has physical dimensions in excess of several inches in at least one direction. The bar composition of this invention is of a shape and size generally known as "facial soap" or "bath soap" sizes. This invention is described in terms of the essential ingredients, discussed below, followed by exemplification and testing of the resulting product.

Surfactant

The surfactant system of this invention may include quaternary ammonium surfactants for their superior lathering ability and skin conditioning affect. Their inclusion is made possible by the low pH of 4–7 of the composition. The quaternary surfactant is typically of the formula:

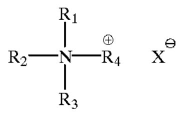

In the general formula, $R_1$, $R_2$, $R_3$ and R4 are hydrogen or alkyl, and at least one of $R_1$–$R_4$ are straight or branched alkyl of at least 8 carbon atoms. In general, the carbon count of $R_1$–$R_4$ should be in excess of 12. These are generally referred to as "fatty quaternary compounds". X is any suitable anion, typically chlorine. Bromine and methosulfate may also be used. These surfactants are present in an amount of 0.1% –5% by weight. Representative quaternary surfactants include behentrimonium chloride (BTAC), stearyl trimethyl ammonium chloride (STAC) and distearyldimonium chloride (DSDC).

In addition to the quaternary surfactant, the claimed invention employs anionic surfactants. The anionic surfactants are present in amounts of about 15–45% by weight, and are combined with the quaternary surfactant to give a total surfactant content of not more than 50% by weight. Preferred total surfactant content includes a combination of quaternary and anionic surfactants in the amount of 20–45% by weight.

A particularly preferred surfactant system includes sodium cocoyl isethionate (SCI) in combination with sodium dodecylbenzene sulfonate (LAS). These materials are advantageously used in about a 4:1 to 6:1 ratio (SCI:LAS). Other combinations of anionic surfactants perform acceptably.

Alternate anionic materials include:

- alkyl (C8–18) sulfates (e.g., sodium lauryl sulfate, sodium ceteryl sulfate, sodium lauryl amide methylene sulfate),
- alkyl (C8–18) ether sulfates (e.g., sodium laureth-x sulfate, x=1 to 12)
- fatty acid soaps (e.g., sodium stearate, sodium laurate),
- sulfated fatty acids (sulfated coconut acid, sulfated stearic acid, sulfated acid palmitic
- sulfated lower alkyl fatty acid esters (sulfated methyl stearate, sulfated ethyl palmitate, sulfated propyl stearate), sulfonated fatty acids (sulfonated coconut acid),
- sulfonated lower alkyl fatty acid esters (sulfonated coconut methyl ester),
- alkyl (C8–18) sulfonates (e.g., sodium C14–16 olefin sulfonate, sodium cocoglyceryl ether sulfonate, sodium laurylsulfoacetate),
- sulfosuccinates (e.g., sodium lauryl sulfosuccinate, disodium laureth sulfosuccinate, disodium cocamido MEA sulfosuccinate),
- alkyl phosphates (sodium stearyl monophosphate, potassium lauryl phosphate),
- taurates (e.g., sodium methyl cocoyl taurate),
- alkyl (C8–18) amino acids, esters, amides and ethers thereof (e.g., acyl glutamates such as sodium cocoyl glutamate, n-lauroyl-β-alanine, alkyl carboxyethylglycinates)
- alkyl ether carboxylates (e.g., sodium laureth-13 carboxylate) and
- sarcosinates (e.g., sodium lauroyl sarcosinate, sodium cocoyl sarcosinate)

These materials may be neutralized with ammonium, sodium, potassium, magnesium, calcium, lithium, or TEA.

Nonionic surfactants such as alcohol ethers (e.g., laureth-3, steareth-6), fatty acid alkanolamides (e.g., cocamide DEA, lauramide MIPA), amine oxides (e.g., lauramine oxide, cocamidopropyl amine oxide), sorbitan esters (e.g., sorbitan laurate, sorbitan oleate, sorbitan isostearate, sorbitan palmitate) and alkyl polyglucosides (e.g., decyl polyglucose, lauryl polyglucose) may be used as well, alone or in combination with anionic surfactants. These materials may be used to increase certain performance attributes such as lather or cleansing. Their inclusion will depend on the performance target of the particular product (e.g., high cleansing as opposed to skin care).

Zwitterionic and other cationic surfactants may also be used. Acceptable surfactant classes are betaines (e.g., cocamidopropyl betaine), sultaines (e.g., cocamidopropyl hydroxysultaine), amidoamine salts (e.g., stearamidopropyl dimethylamine lactate, isostearylamidopropyl dimethylamine lactate), imidazolinium quaternary salts (e.g., lauryl hydroxy ethyl imidazoline) morpholines (e.g., soyaethyl morpholinium ethosulfate) and acylamphoacetates/acylamphopropionates (e.g., sodium lauroamphoacetate, sodium cocoamphopropionate). These surfactants are generally used for their foam building and skin feel improving properties.

Filler

The inventive product employs about 45–80% filler. The function of the filler is to lower the overall cost of the product without imparting negative characteristics. A preferred filler is maltodextrin or a combination of dextrose and maltodextrin. Typical maltodextrins range in dextrose equivalent from 5–25. A preferred range is 5–15. Maltodextrin is a starch hydrozylate obtained by acidic and/or enzymatic starch hydrolysis. Acid hydrolyzed starches may be used as one method of maintaining a slightly acidic pH. This selection gives good wear rate and aesthetics (low stickiness and the product is resistant to cracking on drying). Other carbohydrates, starches and dextrins may be used successfully it they have appropriate binding and solubility characteristics.

Waxy Binder

The composition includes a waxy binder. These are typically present in amounts of 0–20% by weight. These materials optimize wear rate, feel and cracking characteristics. The presence of the quaternary surfactant in the invention allows a wider choice of waxy binder, but the waxy binder must be selected so as to not unduly suppress lathering and foam building properties. A combination of lauric acid and ethylene glycol distearate works well. Additional binders include waxes, such as paraffin, micro-crystalline waxes, triglyceride waxes, ceresin wax, etc. Waxy materials with melting points between 40°–70° C. will generally be acceptable.

Optional Components

Other materials that may be included in the invention include emollients (e.g., mineral oil, avocado oil, petrolatum, fatty acid esters, silicones), skin conditioning polymers (e.g., cationic cellulose, guar and guar derivatives, polyvinyl alcohol and polyvinyl pyrrolidone), colorants/pigments, fragrances and the like. Pigments, preservatives, and fragrances are well known to those of skill in the art and are not further exemplified herein. Selection of the preferred embodiments set forth above will generally result in a mildly acidic pH. The addition of pH modifiers such as citric acid, latic acid or salts thereof may be employed, when necessary, to maintain pH at 4–7, where quaternary surfactants are employed.

Processing

U.S. Pat. No. 5,756,438 gives a specific tableting process that is required to make the personnel cleansing product addressed therein. An important advance in this application is the ability to prepare product using conventional plodding equipment. In plodding equipment generally, mill ribbons or refiner pellets are fed into a plodder where an internal screw forces the product into a compression area that ends in a tapered outlet fitted with a die, through which a log of product (e.g., soap in the prior art) is continuously extruded.

Water or other cooling liquid can be circulated through a jacket surrounding the plodder barrel. The plodder die can be heated to obtain a smooth surface on the extruded soap. The log is cut, cooled, stamped, wrapped and cartonned. These operations may be conducted continuously by machines capable of producing in excess of 300 bars per minute. To facilitate manufacture by plodding equipment, water is incorporated in amounts of 5–15%. To prepare the mill ribbon or pellet for plodding, one of three alternatives may be selected. Melting of the waxy components, followed by mixing with and onto the filler and surfactant, followed by a particle size reduction as is conventional in the art allow for amalgamation, plodding and extruding on conventional soap-type equipment. In the alternative, pellet formation via spray drying (to an appropriate water percent) of a flowable melt of the surfactants, waxy binders and water followed by amalgamation of the filler and other optional components. The pellets are subsequently plodded and extruded on conventional soap equipment may be practiced. In a preferred alternative, all components including water are charged to a mixer (e.g., a high viscosity material mixer such as a sigma blade mixer, a Littlefords® plow mixer or a Processall® mixer). The components are mixed to form a high viscosity paste or dough which can be fed directly to a plodder.

EXAMPLES

In U.S. Pat. No. 5,756,438, examples comparing the invention with then-available commercial products are set forth, showing the superiority of the subject matter addressed therein. As that subject matter is superior to the available compositions, that subject matter forms the basis for comparison herein, and is referred to as control, in the following examples. The examples compare products prepared by the dry mix/extrusion process, spray drying/extrusion process and dough etrusion process, as described above, set forth in Table 1. Table 2 compares performance characteristics of various compositions.

TABLE 1

(wt %)

| | Processing Examples | | | |
|---|---|---|---|---|
| Ingredient | Control | #1 (Dry mix/extrude) | #2 (Spray dried/extrude) | #3 (Dough/extrude) |
| Sodium Cocyl Isethionate | 32.7 | 31.05 | 31.05 | 25.00 |
| Sodium Dodecylbenzene Sulfonate | 5.0 | 4.75 | 4.75 | 4.75 |
| Maltodextrin | 36.8 | 44.38 | 44.38 | 51.69 |
| Dextrose | 16.0 | 0.00 | 0.00 | 0.00 |
| Ethylene Glycol Distearate | 5.0 | 4.75 | 4.75 | 3.00 |
| Lauric Acid | 4.0 | 3.80 | 3.80 | 3.00 |
| Titanium Dioxide | 0.5 | 0.33 | 0.33 | 0.33 |
| Behentrimonium Chloride | 0.0 | 1.39 | 1.39 | 1.40 |
| Water | 0.0 | 8.45 | 8.45 | 9.73 |
| Fragrance | 0.0 | 1.10 | 1.10 | 1.1 |
| | Evaulation | | | |
| Appearance and density | Plastic/more dense than soap/no grit | Plastic/density similar to soap/no grit | Plastic/density similar to soap/no grit | Plastic/density similar to soap/no grit |
| Durability | Acceptable | Acceptable | Acceptable | Acceptable |
| Cracking | Acceptable | Acceptable | Acceptable | Acceptable |
| Lather flash | good | excellent | excellent | excellent |
| Lather quantity | 2 | 1 | 1 | 1 |
| Easily turns in hands | good | excellent | excellent | excellent |
| Ease of removing from counter surface | poor | good | good | good |
| Skin feel/conditioning | good | excellent | excellent | excellent |

Control: High shear blending with heat followed by tabletting of bar.
#1 (Dry mix/Extrude): High shear blending with heat followed by particle size reduction then amalgamation of residual water and fragrance followed by plodding and extrusion.
#2 (Spray dried/extrude): pellet formation via spray drying (to appropriate water %) of a flowable melt of the surfactants, waxy binders and excess water followed by the amalgamation then plodded and extruded.
#3 (Dough/extrude): High shear/heat blending resulting in dough, dough then plodding and extruded
Lather quantity - 5 point scale: 1 = abundant lather, 5 = no lather

TABLE 2

| Ingredients | Soap with BTAC | BTAC 0.1% | BTAC 1.39% | BTAC 4% | DSDC 0.1% | DSDC 1.39% | DSDC 4% | Base without Quat | Base without waxy binders |
|---|---|---|---|---|---|---|---|---|---|
| Soap (sodium tallowate % sodium cocoate) | 94.90 | 0.00 | 0.00 | 0.00 | 0.00 | 0.00 | 0.00 | 0.00 | 0.00 |
| Sodium Cocyl Isothionate | 0.00 | 31.05 | 31.05 | 31.05 | 31.05 | 31.05 | 31.05 | 31.05 | 15.00 |
| Sodium Dodecylbenzene Sulfate | 0.00 | 4.75 | 4.75 | 4.75 | 4.75 | 4.75 | 4.75 | 4.75 | 4.75 |
| Meltodextrim | 0.00 | 44.38 | 44.38 | 44.38 | 44.38 | 44.38 | 44.38 | 44.38 | 69.07 |
| Ethylene Glycol Distearate | 0.00 | 4.75 | 4.75 | 4.75 | 4.75 | 4.75 | 4.75 | 4.75 | 0.00 |
| Lauric Acid | 0.00 | 3.80 | 3.80 | 3.80 | 3.80 | 3.80 | 3.80 | 3.80 | 0.00 |
| Titanium dioxide | 0.00 | 0.33 | 0.33 | 0.33 | 0.33 | 0.33 | 0.33 | 0.33 | 0.33 |
| Fatty Quat* | 4.00 | 0.10 | 1.39 | 4.00 | 0.10 | 1.39 | 4.00 | 0.00 | 1.40 |
| Water | 0.00 | 9.74 | 8.45 | 5.84 | 9.74 | 8.45 | 5.84 | 9.84 | 8.35 |
| Fragrance | 1.10 | 1.10 | 1.10 | 1.10 | 1.10 | 1.10 | 1.10 | 1.10 | 1.10 |
| | | | | | Performance | | | | |
| Lather flash | poor | good | good | fair | good | good | fair | good | fair |
| Lather quantity | 4 | 2 | 2 | 3 | 2 | 2 | 3 | 2 | 3 |
| Lather cream | 5 | 2 | 1 | 1 | 1 | 1 | 1 | 3 | 3 |
| Skin conditioning | No skin conditioning detected | fair | good | good | good | good | good | fair | good |
| Odor stability at 50 C. (2 wks) | Amine odor | ok | ok | ok | ok | ok | ok | ok | ok[a] |
| Appearance stability at 50 C. (2 wks) | Failed | ok | ok | ok | ok | ok | ok | ok | ok[a] |
| pH 1% Solution | 9.7 | 5.1 | 5.1 | 5.1 | 5.1 | 5.0 | 4.8 | 5.0 | 5.1 |

Fatty quat:
BTAC = Behentrimonium Chloride
DSDC = Distearyldimonium Chloride
Lather quantity - 5 point scale: 1 = abundant lather, 5 = no lather
Lather cream - 5 point scale: 1 = Dense rich cream, 5 = open/large bubbles
[a]Stability based on ambient conditions at 6 months.

The inventive subject matter of this application has been described above in both generic terms, and by specific example. Specific identities in the Specification and in the examples are not intended as, and should not be construed as limiting. Variations within the generic classes identified, including other specifically chemical constituents, additives and the like, as well as related process conditions, will occur to those of ordinary skill in the art without the exercise of inventive faculty. Such variations remain within the scope of the invention, unless excluded by the recitations of the claims set forth below.

What is claimed is:

1. A non-soap cleansing bar, having good lathering characteristics, a smooth feel and a resistance to cracking on drying, comprising:

(a) a first surfactant component comprising a quaternary surfactant of the formula

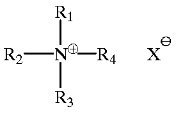

wherein $R_1$, $R_2$, $R_3$ and $R_4$ are each hydrogen or alkyl, and wherein the total number of carbon atoms therein is in excess of 10, and wherein X is a counter anion, said first surfactant component being present in an amount of 0.1–5.0% by weight, (b) a second surfactant component comprising at least one anionic surfactant present in an amount of about 15–45% by weight, (c) a filler component comprising at least one filler selected from the group consisting of non-starch carbohydrates, starches and starch hydrozylates, said filler component being present in amounts of 45–80% by weight, (d) about 0.1–20% by weight waxy binder having a melting point between 40°–70° C., and (e) about 5–20% by weight water, wherein said non-soap cleansing bar has an acidic pH.

2. The non-soap cleansing bar of claim 1, wherein said first surfactant component is present in amounts of 0.1–5.0%.

3. The non-soap cleansing bar of claim 1, wherein said filler is comprised of dextrose and maltodextrin.

4. The non-soap cleansing bar of claim 1, wherein said waxy binder is comprised of a combination of lauric acid and ethylene glycol disterate.

5. The non-soap cleansing bar of claim 1, wherein said at least one anionic surfactant is selected from the group consisting of alkyl sulfates, alkyl ether sulfates, fatty acids, sulfated fatty acids, sulfated fatty acid esters, sulfonated fatty acids, sulfonate lower alkyl fatty acid esters, alkyl sulfonates, sulfosuccinates, alkyl phosphates, taurates, alkyl amino acids, alkyl amino esters, alkyl amino amides, alkyl ether carboxylates, sarcosinates and linear alkyl benzene sulfonates.

6. The non-soap cleansing bar of claim 1, wherein said second surfactant component further comprises at least one of a non-ionic surfactant, a zwitterionic surfactant and an additional cationic surfactant.

7. The non-soap cleansing bar of claim 1, wherein said non-soap cleansing bar further comprises at least one of an emollient, a skin conditioning polymer, a pigment and a fragrance.

8. The non-soap cleansing bar of claim 1, wherein said second surfactant component comprises sodium cocoyl isethionate.

9. The non-soap cleansing bar of claim 8, wherein said second surfactant component further comprises sodium dodecylbenzene sulfonate.

10. The non-soap cleansing bar of claim 1, wherein said non-soap cleansing bar has a pH between 4 and 7.

11. A non-soap cleansing bar, having good lathering characteristics, a smooth feel and a resistance to cracking on drying, comprising:

(a) a first surfactant component comprising 0.1–5.0% by weight behentrimonium chloride, (b) a second surfactant component comprising at least one anionic surfactant present in an amount of about 15–45% by weight, (c) a filler component comprising at least one filler selected from the group consisting of non-starch carbohydrates, starches and starch hydrozylates, said filler component being present in amounts of 45–80% by weight, (d) about 0.1–20% by weight waxy binder having a melting point between 40°–70° C., and (e) about 5–20% by weight water.

* * * * *